United States Patent [19]

Leake

[11] Patent Number: 5,534,573
[45] Date of Patent: Jul. 9, 1996

[54] AMINOTRIAZINE PHOSPHONATES IN PLASTICS

[75] Inventor: Jonathan S. Leake, Coventry, United Kingdom

[73] Assignee: Courtaulds PLC, London, United Kingdom

[21] Appl. No.: 244,728

[22] PCT Filed: Dec. 17, 1992

[86] PCT No.: PCT/GB92/02349

§ 371 Date: Jun. 8, 1994

§ 102(e) Date: Jun. 8, 1994

[87] PCT Pub. No.: WO93/12173

PCT Pub. Date: Jun. 24, 1993

[30] Foreign Application Priority Data

Dec. 18, 1991 [GB] United Kingdom .................. 9126841

[51] Int. Cl.$^6$ ...................................... C08K 5/04
[52] U.S. Cl. .................... 524/100; 523/451; 524/556; 524/560; 524/565; 524/601; 524/606; 544/195; 525/453; 525/417
[58] Field of Search ................................. 524/100, 556, 524/560, 565, 601, 606; 544/195; 523/451; 525/417, 453

[56] References Cited

U.S. PATENT DOCUMENTS

| | | | |
|---|---|---|---|
| 3,011,998 | 12/1961 | D'Alelio | 260/45.2 |
| 3,158,450 | 11/1964 | D'Alelio | 44/63 |
| 3,210,350 | 10/1965 | D'Alelio | 260/248 |
| 3,650,670 | 3/1972 | Tesero et al. | 8/116.3 |
| 3,654,274 | 4/1972 | Chance et al. | 260/249.8 |
| 3,755,323 | 8/1973 | Weil et al. | 528/108 |
| 3,787,407 | 1/1974 | Hendricks | 544/195 |
| 4,107,103 | 8/1978 | Hubner et al. | 528/72 |
| 4,160,795 | 7/1979 | Albright et al. | 524/117 |
| 4,242,288 | 12/1980 | Weil | 521/107 |
| 5,350,848 | 9/1994 | Cipolli et al. | 544/195 |

FOREIGN PATENT DOCUMENTS

| | | |
|---|---|---|
| 2295042 | 7/1976 | France . |
| 49-46635 | 12/1974 | Japan . |

OTHER PUBLICATIONS

Moreau et al., "New Method for Preparing Alkyl (Amino-s-triazinyl) phosphonates", Journal of Chemical & Engineering Data, vol. 15, No. 4, Oct., 1970, pp. 581–583.

T. Masai et al, "Triazine Derivatives", *Chemical Abstracts*, 83 (1):857, Abstract No. 10165K (Jul. 7, 1975).

W. Hewertson et al, "1,3,5–Triazines. Part III. Arbozov Reactions of Chlorotriazines", *J. Chem. Society*, 1670–1675 (1962).

J. Mikroyannidis, "Synthesis, Physical, and Thermal Properties of Linear Poly(dialkoxyphosphinyl-s-Triazines)s", *J. Polymer Science: Part A, Polymer Chemistry*, 26:583–593 (1988).

*Primary Examiner*—Robert E. Sellers
*Attorney, Agent, or Firm*—Howson and Howson

[57] ABSTRACT

Triazine compounds useful as flame retardants have the formula:

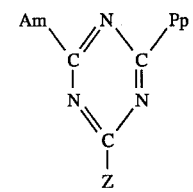

where Am represents an amino group, Pp represents a phosphonate group and Z represents an amino group or a phosphonate group, or are polymers comprising repeating units of the formula:

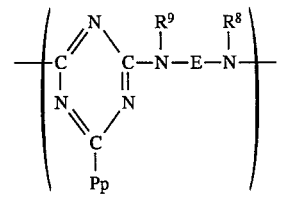

where

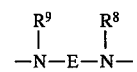

is a diamine residue. The triazine compounds are used as flame retardants in plastics materials, particularly polyurethane foam or artificial fibres, or in intumescent fire protection compositions.

11 Claims, No Drawings

AMINOTRIAZINE PHOSPHONATES IN PLASTICS

FIELD OF THE INVENTION

This invention relates to substituted triazine compounds and to their use. In particular, it relates to sym-triazine (1,3,5-triazine) compounds containing at least one phosphonate, phosphonamidate or phosphonamide group which are generally useful as flame retardants in various organic materials, for example plastics materials such as plastics sheet or film, foamed polymers, moulded plastics articles or fibrous materials such as textiles. Many of the phosphorus-containing triazine compounds have spumescent properties, that is to say they foam at high temperatures and can be used in intumescent coatings or claddings which form an expanded char acting as protective insulation in a fire. Many of the phosphorus-containing triazine compounds are also useful as corrosion inhibitors, for example in surface coatings which inhibit corrosion of metals to which they are applied or which inhibit rust staining.

BACKGROUND OF THE INVENTION

U.S. Pat. No. 3,210,350 describes sym-triazine compounds having one or two of the three ring carbon atoms attached to a phosphonic radical of the formula:

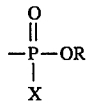

where R represents hydrogen or a saturated hydrocarbon group of up to 12 carbon atoms and X represents -OR or -NR$_2$; the other ring carbon atom(s) are attached to a hydroxy, mercapto, nitro, acyl, acyloxy, amino, alkoxy, aryloxy, cycloalkyloxy, alkylsulpho, arylsulpho, cycloalkylsulpho, ureido, hydrazino, alkyl, aryl or cycloalkyl group. The compounds are stated to be useful as fire retardants, rust inhibitors, chemical intermediates, rust removers, electroplating additives, herbicides, insecticides, ion exchange resins, tanning agents, water-soluble interfacial agents, water-insoluble dispersion agents, detergents, wetting agents, gasoline inhibitors and monomers for vinyl polymerisation and copolymers. U.S. Pat. No. 3,158,450 describes the use of such a compound or a metal derivative thereof as an additive to leaded gasoline to inhibit engine misfiring. U.S. Pat. No. 3,011,998 describes condensation products of such triazine compounds with an aldehyde.

An article by J. P. Moreau and L. H. Chance in "American Dyestuff Reporter", May 1970 at pages 37–38 and 64–65 describes the evaluation of 2-amino-4,6-bis(diethoxyphosphinyl)- 1,3,5-triazine and 2,4-diamino-6-diethoxyphosphinyl- 1,3,5-triazine as possible flame retardant finishes for cotton. An article by the same authors in the same Journal in February 1971 at pages 34–38 describes the evaluation of the formaldehyde derivative of 2,4-diamino-6-diethoxyphosphinyl-1,3,5-triazine as a flame retardant for cotton. U.S. Pat. No. 3,654,274 describes new processes for preparing this compound.

An article by J A Mikroyannidis in J Polymer Science: Part A; Polymer Chemistry, Vol. 26, pages 583–593 (1988) describes linear poly(dialkoxyphosphinyl-sym-triazine)s prepared by interfacial or solution polycondensation reactions of various diamines such as ethylene diamine, hexamethylene diamine or bis(4-aminocyclohexyl) methane with 2-dialkoxyphosphinyl-4,6-dichloro-sym-triazines.

SUMMARY OF THE INVENTION

According to one aspect of the invention a plastics material contains a phosphorus-containing heterocyclic flame retardant and is characterised in that the flame retardant is a sym-triazine compound of the formula:

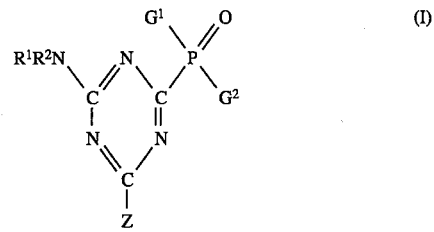

or a polymer comprising repeating units of the formula:

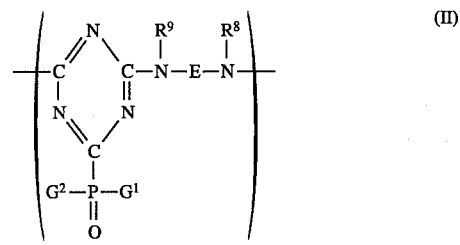

where R$^1$ represents hydrogen, an alkyl or cycloalkyl group having 1 to 12 carbon atoms, an aryl or aralkyl group having 6 to 20 carbon atoms, a heterocyclic group having 2 to 14 carbon atoms and 1 to 4 hetero-atoms selected from N, S and O, or an -NH$_2$, -CONH$_2$ or -NHCONH$_2$ group, and R$^2$ represents hydrogen or an alkyl or cycloalkyl group having 1 to 12 carbon atoms, or R$^1$ and R$^2$ are joined together so that the group R$^1$R$^2$N- is a heterocyclic group having 2 to 14 carbon atoms and 0 to 3 hetero-atoms selected from N, S and O in addition to the N atom bonded to the triazine ring;

G$^1$ and G$^2$ are each independently selected from an -OR$^3$ group, an amine group of the formula -NR$^4$R$^5$, an -OH group or an anionic group -O$^-$ in the form of a metal salt or an amine or ammonium salt, where R$^3$ represents an alkyl or cycloalkyl group having 1 to 12 carbon atoms, and R$^4$ and R$^5$ each independently represent hydrogen or an alkyl or cycloalkyl group having 1 to 12 carbon atoms;

Z represents an amine group of the formula -NR$^6$R$^7$ or a phosphonic group of the formula:

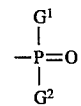

where G$^1$ and G$^2$ are defined as above;

R$^6$ represents hydrogen, an alkyl or cycloalkyl group having 1 to 12 carbon atoms, an aryl or aralkyl group having 6 to 20 carbon atoms or a heterocyclic group having 2 to 14 carbon atoms and 1 to 4 hetero-atoms selected from N, S and O, and R$^7$ represents hydrogen or an alkyl or cycloalkyl group having 1 to 12 carbon atoms, or R$^6$ and R$^7$ are joined together so that the group R$^6$R$^7$N- is a heterocyclic group having 2 to 14 carbon atoms and 0 to 3 hetero-atoms selected from N, S and O in addition to the N atom bonded to the triazine ring;

R$^8$ and R$^9$ each independently represent hydrogen or an alkyl or cycloalkyl group having 1 to 12 carbon atoms, and E represents a divalent organic group having 1 to 20 carbon atoms linked to each -NR$^8$- and -NR$^9$- group through a carbon atom and containing 0 to 3 carbocyclic aromatic rings, 0 or 1 heterocyclic ring having 1 to 4 hetero-atoms selected from N, S and O, and 0 to 2 ether, ester, amide, amine or urethane linkages, or $R^8$ and $R^9$ are joined together so that the group

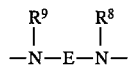

is a heterocyclic group having 3 to 14 carbon atoms and 0 to 2 hetero-atoms selected from N, S and O in addition to the N atoms bonded to triazine rings.

The compounds and polymers of formulae (I) and (II), which are essentially halogen-free, are at least as effective as present commercial flame retardants containing halogen; halogenated compounds are becoming regarded as environmentally undesirable for some uses.

The plastics material can be in the form of a foam, sheet, film, filament or moulded article. It can be thermoplastic or thermoset. The flame retardants used in the invention are particularly suitable for incorporation in polyurethane foam used in furniture and in seats for cars, trains or aircraft; the flame retardant can be mixed with the polyol which is reacted with polyisocyanate to form the polyurethane foam.

The invention thus includes a polyol composition comprising a polyol selected from polyether and polyester polyols suitable for preparing polyurethane foam, said polyol composition containing as flame retardant a phosphorus-containing sym-triazine compound of the formula:

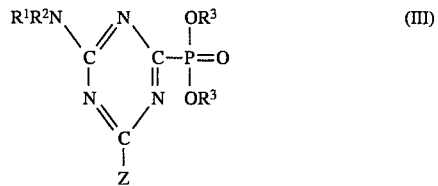

in which the groups $R^1$, $R^2$, $R^3$ and Z are defined as above but $R^3$ preferably represents an alkyl group having 1 to 6 carbon atoms, the groups $R^3$ being the same or different, and Z is preferably an amine group of the formula $-NR^6R^7$ or a phosphonate group of the formula $-P(OR^3)_2O$. The invention also includes a process for the production of polyurethane foam of reduced flammability in which such a polyol composition is reacted with a polyisocyanate in the presence of a foaming agent.

The invention also includes an artificial fibre having a flame retardant dispersed throughout the fibre-forming material, characterised in that the flame retardant is a substantially water-insoluble phosphorus-containing sym-triazine compound of formula (I) or polymer of formula (II). The invention also includes a process for the production of artificial fibre of reduced flammability by incorporating such a flame retardant of formula (I) or (II) in a spinning dope and extruding the dope through a spinneret to form filaments.

The invention also includes an intumescent fire protection composition comprising a carbon source capable of providing a char, a spumific agent and sources of nitrogen and phosphorus, characterised in that a compound of formula (I), in which at least one of the groups $G^1$ and $G^2$ is an anionic group $-O^-$ in the form of an ammonium, amine or metal salt, acts as a spumific agent as well as providing a source of nitrogen and phosphorus.

Certain of the compounds of formula (I) are new compounds. Thus according to another aspect of the invention a phosphorus-containing flame retardant is a sym-triazine compound which is liquid at ambient temperature, is soluble in a polyether polyol (for example a polyoxypropylene triol of molecular weight 3500) and has the formula (III) above, in which the group $R^1$ contains at least two carbon atoms.

Certain of the polymers of formula (II) are new, particularly those in which at least one of the groups $R^8$ and $R^9$ is other than hydrogen and those in which E contains at least one aromatic or heterocyclic ring, and such compounds form a further aspect of the invention.

DETAILED DESCRIPTION

The compounds of formula (I) can be prepared with a wide range of physical properties by varying the groups $R^1$, $R^2$, $G^1$, $G^2$ and Z, in particular by changes in the number and type of alkyl substituents in $-NR^1R^2$ and $-PO(OR^3)_2$ groups. The compounds of formula (I) can for example be high-boiling liquids or solids of low or high melting point, and can have varying solubility in organic solvents. The ratio of nitrogen to phosphorus atoms can be varied in the compounds of formula (I), particularly by varying the nature of the group Z. The optimum ratio of nitrogen to phosphorus atoms required for greatest flame retardancy may be different for different flame-retardant uses. Polymers of formula (II) can be produced with a high or low melting point and glass transition temperature.

The compounds of formula (I) in which $R^1$ represents an alkyl or cycloalkyl group having 1 to 12, preferably 1 to 6, carbon atoms, an aryl (e.g. phenyl or alkyl-substituted phenyl) or aralkyl group having 6 to 20 carbon atoms, or a heterocyclic group having 2 to 14 carbon atoms and 1 to 4 hetero-atoms selected from N, S and O, particularly the phosphonate esters of formula (III), are more easily processed than the compounds in which $R^1$ and $R^2$ (and $R^6$ and $R^7$ if present) are both hydrogen. These compounds having an N-organo substituent, particularly those in which $R^1$ is an alkyl group, generally have lower melting points and increased solubility in organic solvents. For example, the compounds in which $R^1$ represents an alkyl group are soluble in the polyols (polyether or polyester polyols) used in polyurethane foam manufacture. They are generally soluble in most common organic solvents except alkanes, for example alcohols, cyclic ethers, aromatic ethers, diethers, ether-alcohols, ketones, nitriles and aromatic hydrocarbons. The compounds of formula (I) which contain no amine hydrogen atoms, in particular those in which $R^1$ and $R^2$ (and $R^6$ and $R^7$ if present) are all alkyl or cycloalkyl groups, are soluble in alkanes as well as the above solvents. The compounds in which Z represents $-NR^6R^7$ and $R^1$, $R^2$, $R^6$ and $R^7$ all represent hydrogen are soluble only in highly polar organic solvents such as dimethyl sulphoxide or N-methylmorpholine oxide. Some of the compounds of formula (I) are liquids, particularly those in which both $R^1$ and $R^2$ (and $R^6$ and $R^7$ if present) are alkyl groups. Liquid flame retardants are often preferred in polyurethane foam manufacture. Other compounds of formula (I) which are liquid are the diphosphonates in which Z represents a $-PO(OR^3)_2$ group and compounds in which at least one of the groups $R^1$ and $R^2$ is a long chain alkyl group having at least 6, particularly 8 to 12, carbon atoms. Compounds of formula (I) in which Z is an $-NR^6R^7$ amino group which is different from the $-NR^1R^2$ amino group, for example where $-NR^1R^2$ is an alkylamino group and $-NR^6R^7$ is a dialkylamino group, or where the alkyl group(s) of $-NR^6R^7$ are different from the alkyl group(s) in $-NR^1R^2$, have a lower melting point than compounds with similar amino groups and may be liquid at ambient temperature. Examples of preferred alkyl and aryl groups for $R^1$ are ethyl, isopropyl, methyl, hexyl and phenyl. $R^2$ can for example be hydrogen or a methyl or ethyl group so that preferred groups $-NR^1R^2$ are diethylamino, isopropylamino, dimethylamino, ethylamino or n-butylamino.

The compounds of formula (I) in which Z represents an -NR⁶R⁷ group generally have a lower water solubility than the compounds in which Z represents a -PO(OR³)₂ group. The compounds in which Z represents an -NR⁶R⁷ group and at least one of the groups R¹, R², R⁶ and R⁷ is an alkyl or other hydrocarbyl group have very low water solubility and resist washing out of a substrate such as a foam or textile material. Within the class of compounds of formula (I) in which Z represents a -PO(OR³)₂ group, those compounds in which R¹ and R² are both alkyl or other hydrocarbyl groups have lower water solubility (generally less than 5% by weight when both groups R³ are ethyl). Compounds in which Z represents a -PO(OR³)₂ group and R¹ represents a phenyl or other aryl group also have lower water solubility and may be preferred flame retardants if an increased ratio of phosphorus to nitrogen atoms is required.

The compounds of formula (I) in which Z represents a -PO(OR³)₂ group and in which R³ is an alkyl group having more than two carbon atoms, for example where R³ is an isopropyl group or an n-butyl group, have markedly reduced water solubility and are generally liquid when at least one of R¹ and R² is an alkyl group. Such compounds, particularly those in which R¹ and R² are both alkyl groups, are another class of preferred flame retardants having an increased ratio of phosphorus to nitrogen atoms.

Polyurethane foams are generally produced by reacting a polyol composition with a polyisocyanate in the presence of a foaming agent. The polyol is generally a polyether polyol or polyester polyol. The polyol is usually a polyether polyol of functionality 2.5–3.5 for production of a flexible foam, for example a polyether triol of molecular weight 3000–6000 prepared by the addition of propylene oxide and optionally ethylene oxide to a polyalcohol such as glycerol or to an aminoalcohol or polyamine. The polyether triol can optionally contain a dispersion of another polymer, for example a polyurea or a styrene/acrylonitrile copolymer, to produce a high-resilience flexible foam. For production of a rigid foam, a more highly functional polyol, for example of average functionality 4 to 5, of lower equivalent weight, for example 100–150, is used. The polyisocyanate is usually toluene diisocyanate (TDI) for production of flexible foam, and it may be a TDI prepolymer or diphenylmethane-4,4'-diisocyanate or an oligomer thereof for rigid foam production. The foaming agent can be a volatile compound such as a halocarbon, but for flexible foams it is usually water, which reacts with isocyanate groups to release $CO_2$. The foam-forming composition also generally contains a surfactant and catalysts and may contain other additives; all these are generally premixed with the polyol.

The flame retardant is preferably dissolved in the polyol. Particularly preferred flame retardants for use in polyurethane foam, for example for mixing with a polyether or polyester polyol in the above process, are those of the formula:

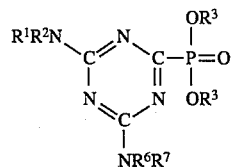

in which at least one of the groups R¹ and R² is an alkyl group, at least one of the groups R⁶ and R⁷ is an alkyl group, and the total number of carbon atoms in the groups R¹, R², R⁶ and R⁷ is 3 to 8 carbon atoms; compounds within this definition in which the groups -NR¹R² and -NR⁶R⁷ are different may be especially preferred. Alternative preferred flame retardants are those of the formula:

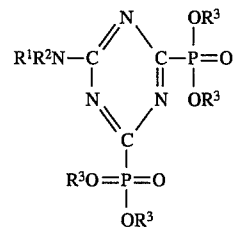

in which R¹ and R² are each alkyl groups having 6 to 12 carbon atoms.

Examples of preferred flame retardants are: Diethyl 2,4-bis(isopropylamino)-1,3,5-triazine-6-phosphonate, diethyl 2,4-bis(n-butylamino)-1,3,5-triazine-6-phosphonate, diethyl 2,4-bis(diethylamino)-1,3,5-triazine-6-phosphonate, di-ethyl 2-n-butylamino-4-diethylamino-1,3,5-triazine-6-phosphonate, tetraisopropyl 2-diethylamino-1,3,5-triazine-4,6-diphosphonate, tetraisopropyl-2-dimethylamino-1,3,5-triazine-4,6-diphosphonate and diethyl 2,4-bis(N-methyl-N-phenyl-amino)-1,3,5-triazine-6-phosphonate.

The compounds of the formula (I) in which R¹ and R² are joined, so that -NR¹R² is a heterocyclic group such as pyrrolidino, piperidino or morpholino and in which Z represents a -PO(OR³)₂ group are readily soluble in water and are useful if a water-soluble flame retardant is required, for example for application from an aqueous medium to a plastics substrate which does not encounter water in use. The compounds of formula (I) in which Z represents an -NR⁶R⁷ group and in which R¹ and R² are joined and R⁶ and R⁷ are joined, so that -NR¹R² and -NR⁶R⁷ represent heterocyclic groups, are however of very low solubility in water and are among the preferred flame retardants for use in a substrate which may encounter water in use.

Although many of the flame retardants of the invention are especially suitable for use in polyurethane foam, they are highly effective flame retardants in substantially all polymers which contain oxygen or nitrogen, for example polyesters, polyamides, acrylic ester polymers, vinyl ester polymers, nitrile polymers such as polyacrylonitrile and unfoamed polyurethanes, and they can also be used as flame retardants in other polymers such as polyolefins or polystyrene. The flame retardants of the invention can be used at 0.1–50% by weight based on the plastics material. In general, at least 0.5% by weight and preferably at least 1% is used to obtain a significant effect. The amount of flame retardant is preferably less than 20% by weight, and most preferably less than 10%, based on the plastics material. When the flame retardant is incorporated in a polyol composition for producing polyurethane foam, it preferably forms 1.5 to 15% by weight of the polyol composition.

The flame-retardant compounds of formula (I) can in general be prepared from cyanuric chloride (2,4,6-trichlorotriazine) by reaction with an appropriate derivative of phosphorous acid, followed by reaction with an amine. For example, cyanuric chloride can be reacted with a trialkyl phosphite of the formula (R³O)₃P in a molar ratio of 1:1, 1:2 or 1:3 to produce a triazine having 1, 2 or 3

phosphonate ester substituents with 2, 1 or 0 remaining chlorine substituents, i.e. a dialkyl 2,4-dichloro-1,3,5-triazine-6-phosphonate, a tetraalkyl 2-chloro-1,3,5-triazine-4,6- diphosphonate or a hexaalkyl 1,3,5-triazine-2,4,6-triphosphonate. The reaction is carried out in an organic solvent, for example an aromatic hydrocarbon such as benzene, toluene or xylene, in the absence of moisture, preferably at an elevated temperature in the range 50°–150° C. The reaction can be catalysed by a catalyst such as sodium iodide. A catalyst is preferably used if the trialkyl phosphite is a secondary alkyl phosphite such as triisopropyl phosphite, allowing complete reaction at 120° C. without decomposition of the product. Alkyl chloride $R^3Cl$ is evolved as by-product; it is most convenient if the alkyl chloride $R^3Cl$ can be removed from the reaction mixture, for example if the alkyl chloride $R^3Cl$ has a lower boiling point than the solvent. The reaction with trimethyl or triethyl phosphite proceeds readily at 120° C. in toluene. Reaction with tri-n-butyl phosphite is preferably at 140° C. in xylene. However, it is preferred in most cases that $R^3$ contains at least 2 carbon atoms, since the methyl phosphonate groups react differently with amines compared to other alkyl phosphonate groups.

If the trialkyl phosphite $P(OR^3)_3$ is unavailable or too expensive, it is possible to prepare the phosphonate by transesterification of a triazine phosphonate which can be made readily. For example, hexaisopropyl triazine triphosphonate can be prepared by reacting hexamethyl triazine triphosphonate with excess isopropanol.

The dialkyl 2,4-dichlorotriazine-6-phosphonate, tetraalkyl 2-chlorotriazine-4,6-diphosphonate and hexaalkyl triazinetriphosphonate can each react with ammonia, or a primary or secondary amine $R^1R^2NH$ to introduce primary, secondary or tertiary amino groups -$NR^1R^2$ respectively. The reaction may be carried out in an organic solvent, for example an aromatic hydrocarbon as described above, at a temperature in the range from −20° to 150° C., preferably at at least −10° C. and below 100° C. In many cases the reaction is preferably carried out by addition of the amine or ammonia to the triazine phosphonate, or vice versa, at a temperature in the range −10° C. to 0° C. The reaction can then be completed by allowing the reaction mixture to warm to 0° C. and above, with heating to 50° C. or above if necessary. The amino groups replace the chloro groups on the triazine ring more readily than they replace the phosphonate ester groups, so that reaction of a dialkyl dichlorotriazine phosphonate with at least 2 moles of amine or ammonia per mole of phosphonate will produce a product substantially free from chlorine, as will reaction of a tetraalkyl chlorotriazine-diphosphonate with at least an equimolar amount of amine or ammonia. The amine or ammonia can also replace phosphonate ester groups in a triazine ring having no chloro-substituents. Thus, cyanuric chloride can be reacted with 3 moles of trialkyl phosphite to produce a hexaalkyl triazinetriphosphonate followed by reaction with an amine or ammonia. Excess trialkyl phosphite can be used but is not recommended as it makes isolation of the hexaalkyl triazinetriphosphonate more difficult.

Removal of successive phosphonate ester groups by an amine or ammonia generally requires increasingly forcing conditions, with the single phosphonate ester group in a 2,4-diaminotriazine-6-phosphonate being very hard to replace. A hexaalkyl triazinetriphosphonate, for example, will react with a primary alkyl amine at room temperature or at elevated temperatures below 100° C. to replace two phosphonate ester groups by secondary amine groups. A hexaalkyl triazinetriphosphonate will react with a secondary dialkyl amine at room temperature to replace only one phosphonate ester group by a tertiary amino group. The 2,4-bis(alkylamino)-triazine-6-phosphonate, in the former case, and the 2,4-dialkylamino-triazine-4,6-diphosphonate, in the latter case, are each produced in high yield. At temperatures of 50° C. and above, for example 50°–100° C., the secondary amine will replace two phosphonate ester groups to form primarily a 2,4-bis(dialkylamino)-triazine-6-phosphonate. This reaction may require the use of excess amine and an extended reaction period, for example at least 24 hours at 60° C.

When a primary aromatic amine such as aniline is reacted with a hexaalkyl triazine triphosphonate, only one phosphonate ester group is replaced at room temperature, forming a 2-arylamino-triazine-4,6-diphosphonate in high yield. When a secondary alkyl aryl amine such as N-methylaniline is reacted with a hexaalkyl triazine triphosphonate, the reaction generally proceeds at room temperature to replace two phosphonate ester groups, and high yields of 2,4-bis(alkyl aryl amino)-triazine-6-phosphonate can be produced at temperatures of 30°–60° C.

A heterocyclic amine such as pyrrolidine, morpholine or piperidine reacts readily with a hexaalkyl triazine triphosphonate, replacing two phosphonate groups to produce for example a 2,4-dipyrrolidino-triazine-6-phosphonate in high yield at room temperature.

The amount of amine required for the above reaction is generally more than the stoichiometric amount required to substitute -$NR^1R^2$ groups on the triazine ring, since base is required to neutralise chloride or phosphite groups displaced from the triazine ring. The same amine can act as both nucleophile and base. For example, the reaction with a chlorotriazine Tz-Cl can be represented by the equation:

$$2R^1R^2NH+Tz\text{-}Cl \rightarrow R^1R^2N\text{-}Tz+R^1R^2N^+H_2Cl^-$$

The reaction to displace a phosphonate ester group from a triazine-phosphonate Tz-$PO(OR^3)_2$ is generally according to the equation:

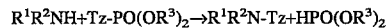
$$R^1R^2NH+Tz\text{-}PO(OR^3)_2 \rightarrow R^1R^2N\text{-}Tz+HPO(OR^3)_2$$

but some amine is consumed by reaction with the dialkyl phosphite co-product according to the equation:

$$HPO(OR^3)_2+R^1R^2NH \rightarrow HPO(OR^3)O^-\ R^1R^2N^+H_2+R^3OH$$

Excess amine is preferably used, although less is required than for reaction with a chlorotriazine. The amine phosphite by-product $HPO(OR^3)O^-\ R^1R^2N^+H_2$ can readily be removed from the desired aminotriazine phosphonate, since the by-product is readily soluble in both water and organic solvents.

As an alternative to the use of excess of the amine $R^1R^2NH$, this amine can be used in conjunction with a tertiary amine such as triethylamine. Use of a tertiary amine is preferred when it is desirable to avoid excess of the substituting amine, for example when the amine $R^1R^2NH$ is expensive, or is involatile or of low volatility, or when different amines $R^1R^2NH$ and $R^6R^7NH$ are successively employed to introduce dissimilar substituents. Use of a tertiary amine is also preferred when the amine $R^1R^2NH$ is only a weak nucleophile and/or a weak base, for example an aromatic amine such as aniline. The tertiary amine is generally used in an equimolar amount to the amine $R^1R^2NH$ when reacting with a chlorotriazine, but it can be used in catalytic amounts, for example 10–50 mole % based on $R^1R^2NH$, when reacting with a triazinetriphosphonate. The reaction of $R^1R^2NH$ with a chlorotriazine phosphonate can alternatively be carried out in a 2-phase aqueous/organic solvent system using an inorganic base in the aqueous phase and a phase transfer catalyst.

The dialkyl dichlorotriazinephosphonate, tetraalkyl chlorotriazinediphosphonate or hexaalkyl triazinetriphosphonate can be reacted with two amines, of the general formula $R^1R^2NH$ and $R^6R^7NH$, respectively, either simultaneously or successively to produce compounds of formula (I) in which Z is a group $-NR^6R^7$ which is different from $-NR^1R^2$. If successive reaction is used, it may be more convenient to use the more reactive amine in the second part of the reaction, since substitution of one phosphonate group by amino reduces the reactivity of the triazine. For example a hexaalkyl, e.g. hexaethyl, triazine triphosphonate can be reacted with an aromatic primary amine such as aniline to introduce one anilino group followed by reaction with a heterocyclic amine such as pyrrolidine to produce diethyl 2-anilino-4-pyrrolidino- 1,3,5-triazine-6-phosphonate. Hexaethyl triazine triphosphonate can be reacted with an equimolar amount of n-butylamine to introduce one n-butylamino group followed by reaction with diethylamine at elevated temperature to produce diethyl 2-n-butylamino-4-diethylamino-1,3,5-triazine-6-phosphonate.

Some of the above reactions are set out in the following reaction scheme; the reactions with amine shown are the predominant reactions at room temperature:

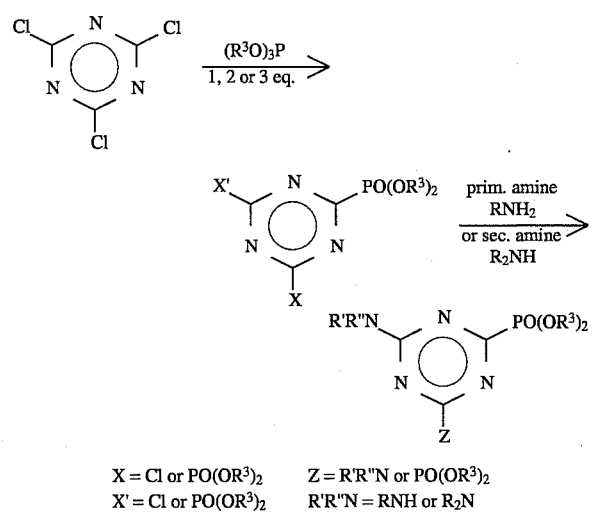

$X = Cl$ or $PO(OR^3)_2$   $Z = R'R''N$ or $PO(OR^3)_2$
$X' = Cl$ or $PO(OR^3)_2$   $R'R''N = RNH$ or $R_2N$

In the above reaction schemes, the group $R^3$ preferably has at least two carbon atoms and the reaction scheme applies most accurately to the case where $R^3$ is ethyl (use of triethyl phosphite). When the group $R^3$ is methyl, the tetramethyl aminotriazine diphosphonate of the formula

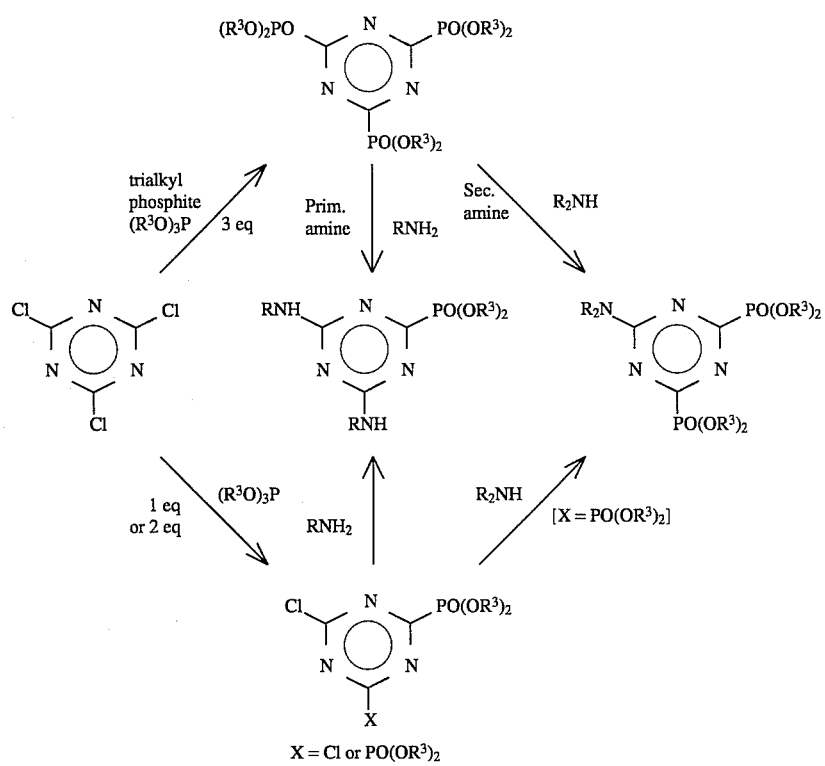

$X = Cl$ or $PO(OR^3)_2$

Use of the symbol R means a hydrocarbon group, particularly an alkyl group, (the groups R may be the same or different). This scheme may be summarised more succinctly as follows:

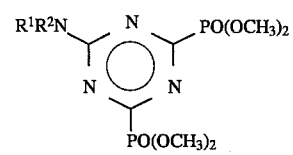

can be formed by the above reaction scheme using a primary or secondary amine $R^1R^2NH$ with strict avoidance of excess amine. In the presence of excess amine or ammonia the phosphonate ester group reacts at least partly with the amine or ammonia ($R^1R^2NH$) to form phosphonate salt groups of the formula:

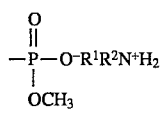

The following phosphonate salt compounds have been prepared by the method described above:

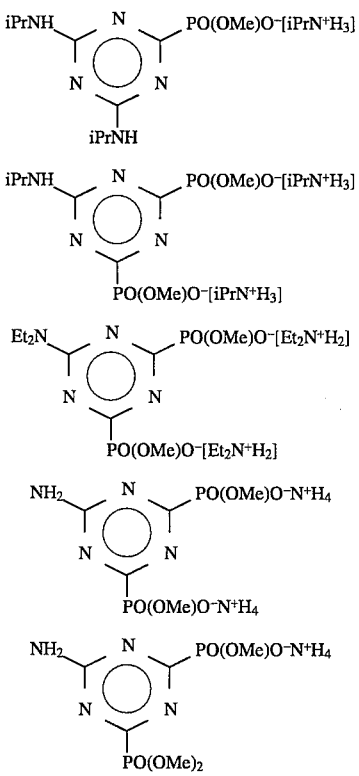

where Me= methyl, Et=ethyl and iPr=isopropyl.

These aminotriazine compounds containing ammonium or substituted ammonium phosphonate salt groups are effective flame retardants, but they cannot be mixed with a polyol in the preparation of polyurethane foam because the salts cause foam to collapse. The salts generally have lower solubility in organic solvents and higher water solubility than the corresponding phosphonate esters. The aminotriazine compounds containing ammonium or substituted ammonium phosphonate salt groups do however show intumescent behaviour, foaming at temperatures in the range 100°–400° C., and they can be used in intumescent fire protection products such as coatings, claddings or fire barriers.

Aminotriazine compounds containing ammonium phosphonate salt groups can also be formed by the reaction of a hexa (primary alkyl) triazine triphosphonate (that is, where $R^3$ is a primary alkyl group having at least 2 carbon atoms) with aqueous ammonia. Whereas hexamethyl triazine triphosphonate reacts with ammonia under aqueous or anhydrous conditions to form an ammonium phosphonate salt, a higher hexa (primary alkyl) triazine triphosphonate such as the ethyl or n-butyl ester will react with anhydrous ammonia to form a dialkyl diaminotriazine phosphonate, but with aqueous ammonia to form a phosphonate salt. A hexa (secondary alkyl) triazine triphosphonate will react with either anhydrous or aqueous ammonia to form mainly a tetra (secondary alkyl) aminotriazine diphosphonate at ambient temperature and a di(secondary alkyl) diaminotriazine phosphonate if heated.

The various reactions of different hexaalkyl triazinetriphosphonates with ammonia are summarised as follows:

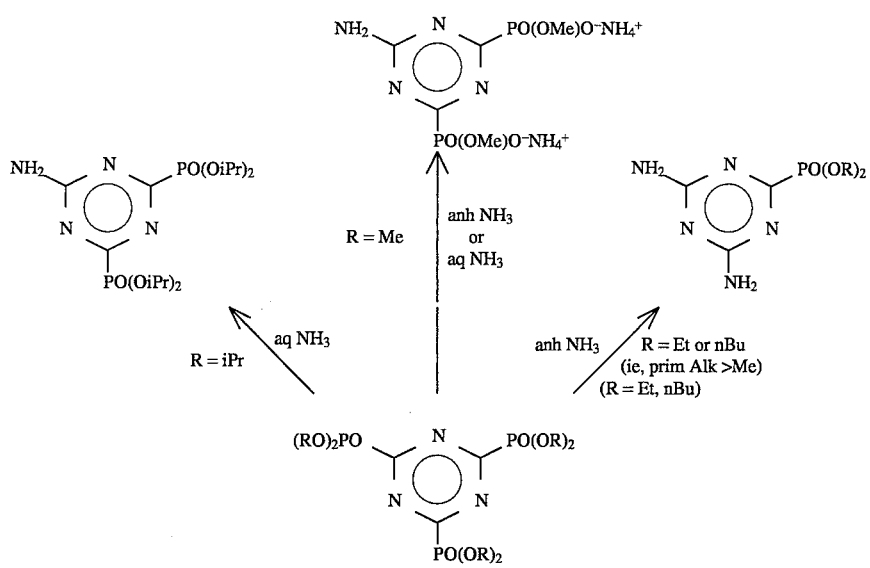

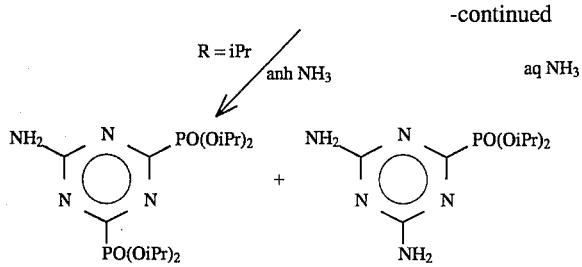
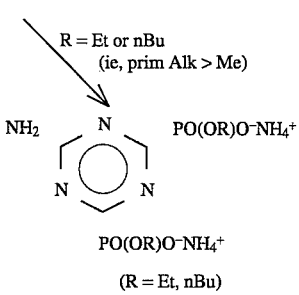

(R = Et, nBu)

where anh. means anhydrous and aq. means aqueous.

A hexa(secondary alkyl) triazine triphosphonate is preferred for reaction with amino compounds $R^1R^2NH$ which are readily available only as a gas or aqueous solution. Examples of such amino compounds are ammonia, methylamine, dimethylamine, ethylamine, hydrazine, urea and semicarbazide. For example, aqueous hydrazine reacts with hexaisopropyl triazine triphosphonate in isopropanol to produce tetraisopropyl 2-hydrazinotriazine diphosphonate. Urea and semicarbazide will react similarly to introduce respectively -NHCONH$_2$ and -NHNHCONH$_2$ groups bonded to the triazine ring.

The polymers of formula (II) can be prepared by the reaction of a phosphonate-substituted triazine with a diamine $HR^8N$-E-$NR^9H$ containing two amino groups selected from primary and secondary amino groups. The phosphonate-substituted triazine can be the reaction product of cyanuric chloride with an equimolar amount of a phosphite, the reaction product having the formula:

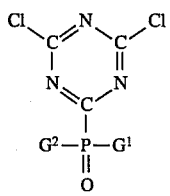

for example a dialkyl dichlorotriazine phosphonate, or alternatively it can be a fully phosphonated compound such as a hexaalkyl triazinetriphosphonate where the groups $G^1$ and $G^2$ are -$OR^3$ groups in which $R^3$ is alkyl, preferably ethyl. The diamine can be a diprimary amine, forming polymers where the groups $R^8$ and $R^9$ are both hydrogen. Polymers where the linking group E contains at least one arylene or heterocyclic moiety have the highest flame resistance. The linking group E can for example be an arylene, diarylene, triarylene, arylenedialkylene, or alkylenediarylene group. The diamine can alternatively be a disecondary amine, forming polymers where the groups $R^8$ and $R^9$ are the same or different alkyl or cycloalkyl groups, or a primary secondary diamine, forming polymers in which the group $R^8$ is alkyl and the group $R^9$ is hydrogen. An alternative type of secondary amine group is one in which the amine nitrogen atom forms part of a heterocyclic ring. If a heterocycle containing two secondary amine nitrogen atoms such as piperazine is used, a polymer is formed in which $R^8$ and $R^9$ are joined together so that

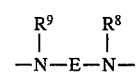

is a divalent heterocyclic group such as piperazin-1,4-diyl. If only one of the amine nitrogen atoms (say $R^8$) is in the heterocyclic ring, a polymer is formed in which

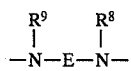

is a heterocyclic group, for example piperidin-1,4-diyl from 4-amino-piperidine. Examples of diamines of the formula $HR^8N$-E-$NR^9H$ are ethylene diamine, meta-phenylene diamine, para-phenylene diamine, propane-1,2-diamine, N-methyl-ethylene diamine, N-methyl-propane-1,3-diamine, N,N'-dimethyl-ethylene diamine, N,N'-dimethyl-propane- 1,3-diamine, butane-1,4-diamine, meta- or para-xylylene diamine, methylenebisaniline, 2,4-tolylene diamine, piperazine, (1,2-diaminoethyl)-benzene, 4-amino-piperidine, bis(2-aminoethyl)ether, a diaminopyrimidine such as 4,6-diaminopyrimidine or 2,4-diamino-6-hydroxy-pyrimidine, or melamine. When the groups $R^8$ and $R^9$ are different or the bridging group E is unsymmetrical, the repeating units of formula (II) can be arranged in head-to-tail or head-to-head configuration or a random mixture thereof; we believe that random polymerisation generally occurs.

Polymers in which $R^8$ and $R^9$ are other than hydrogen have increased solubility in organic solvents compared to polymers containing >NH groups, and polymers in which the linking group

is a heterocyclic ring are soluble in most polar organic solvents. For example, poly (ethylene diamino triazine phosphonate) is soluble in highly polar organic solvents such as dimethyl sulphoxide or N-methylmorpholine oxide. Poly (piperazino triazine phosphonate ester) is soluble in the above solvents and additionally is readily soluble in chloroform, dichloromethane, methanol, acetone and acetonitrile. Moreover, the polymer consisting of triazine rings linked by heterocyclic rings such as piperazine has increased compatibility with other organic polymers such as polyesters or polyamides, facilitating blending of the flame retardant of formula II into a fibre-forming polymer composition.

Another type of polymer having increased solubility in organic solvents and increased compatibility with fibre-forming and other polymers is a triazine phosphonate polymer with alternate aromatic diamine and heterocyclic diamine bridging groups. This can be produced by the successive reaction of hexaalkyl, e.g. hexaethyl, triazine triphosphonate with an aromatic diamine such as m- or p-phenylene diamine and then with a heterocyclic diamine such as piperazine or a substituted piperazine. The phenylene diamine will react with the triazine triphosphonate to produce a compound of the formula:

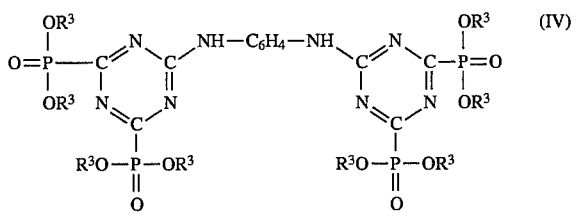
(IV)

but will not readily react further to replace a second phosphonate group on the triazine ring by an amino group. The intermediate (IV) will however react with piperazine to produce a polymer of the formula:

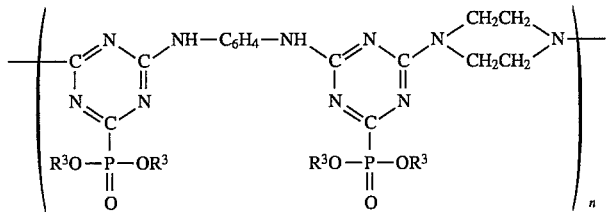

The diamine $HR^8N-E-NR^9H$ is preferably used in conjunction with a tertiary monoamine such as triethylamine. This avoids the premature termination of polymer chains with salts of the diamine such as $-Tz-NH-E-N^+H_3Cl^-$ or $-Tz-NH-E-N^+H_3\ HPO(OR^3)O^-$, since the tertiary amine will form salts more readily and displace the diamine in any salt groups formed.

The polymer (II) according to the invention can be a segmented copolymer in which poly(aminotriazine phosphonate) segments are incorporated in another polymer. For example, an amino-tipped polymer can be reacted with excess of a dichlorotriazine-phosphonate or triazine-triphosphonate, and the product reacted with a diamine $HR^8N-E-NR^9H$.

The polymers of formula (II) can be used as flame retardants in the same way as the compounds of formula (I); in particular they can be added to a polyol during the manufacture of polyurethane foam. The polymer of formula (II) can be incorporated in artificial fibres to impart flame resistance. It can for example be melt-blended with a polyamide, polyester or polyolefin in the formation of melt-spun synthetic fibres. Alternatively, the polymer of formula (II) can be mixed into a spinning dope which is a solution of cellulose in a tertiary amine N-oxide such as N-methylmorpholine N-oxide and extruded into an aqueous bath to form flame-resistant solvent-spun cellulose filaments. When thus incorporated into artificial fibres, the polymers of formula (II) are highly resistant to washing out and impart durable flame resistance. The proportion of (II) in the fibres is preferably at least 2% by weight, for example 5–25%.

The polymers of formula (II) can alternatively be used alone as flame-resistant plastics material. They can be extruded to form fibres or films or moulded, for example by injection, extrusion, blow or compression moulding, to produce flame-resistant moulded articles.

Compounds or polymers containing more than one phosphonate group are generally useful in inhibiting corrosion of metals or for any other use requiring complexing of metals as a chelate. The polymers of formula (II) are particularly useful in this respect. They can be incorporated into paints for surface coating either as a polymer miscible with the binder polymer of the paint or as an insoluble material forming part of the pigment component of the paint. The polymer can for example form 2–60% by weight, preferably 5–40% by weight, of the binder component of the paint, or it can form 2–100% by weight, preferably from 5 up to 50 or 80% by weight, of the pigment component of the paint.

The invention is illustrated by the following Examples.

EXAMPLE 1

Diethyl 2,4-bis(isopropylamino)-1,3,5-triazine-6-phosphonate

To a stirred solution of hexaethyl 1,3,5-triazine- 2,4,6-triphosphonate (29.34 g, 0.06 mol) in toluene (90 ml), cooled at $-2°$ C. and protected from atmospheric moisture, was added dropwise over 40 minutes a solution of isopropylamine (21.24 g, 0.36 mol) in toluene (45 ml). The resulting solution was stirred for 1 hour at 0° C., and then allowed to react for a further 3 days at 20° C. with stirring. Removal of solvent, and drying at 95° C./1 mm, gave a pale yellow solid (21.98 g). A solution of the solid in dichloromethane was extracted with water and dried ($Na_2SO_4$). Removal of solvent, and drying at 95° C./1.5 mm, gave diethyl 2,4-bis(isopropylamino)- 1,3,5-triazine-6-phosphonate (19.49 g, 98%), identified by $^1$H-NMR, $^{13}$C-NMR and FT-IR. Recrystallisation from diisopropyl ether gave the analytical sample (14.00 g, 70%) as a white solid, mp 97.0°–98.5° C.

$^1$H-NMR: δ($CDCl_3$) 1.22 (12H, d, J=6 Hz, $Me_2CH$-N), 1.38 (6H, t, J=7 Hz, $MeCH_2$O-P), 4.04–4.31 (6H, overlapping multipiers, $Me_2CH$-N and Me-$CH_2$-O-P), 5.08–5.19 ($^1$H, broad doublet, NH), 5.29–5.31 (1H, broad doublet, NH);

$^{13}$C-NMR: δ($CDCl_3$) 16.0 (s, Me$CH_2$O-P), 22.0 and 22.4 (0.75:0.25, $Me_2CH$-N), 41.8 and 42.1 (0.2:0.8, $Me_2CH$-N), 63.0 and 63.3 (0.8:0.2, Me-$CH_2$-O-P), 163.7 (d, $J_{PCNC}$=20 Hz, triazine ring carbons with nitrogen substituents), 169.2 (d, $J_{PC}$=266 Hz, triazine ring carbon with phosphorus substituent);

FT-IR: $v_{max}$ (neat) 3265, 3100, 2975, 2935, 2875, 1600, 1530, 1265, 1060, 1030 $cm^{-1}$.

(Analysis: Found C, 47.18; H, 7.91; N, 20.90; P, 9.00. $C_{13}H_{26}N_5O_3P$ requires C, 47.12; H, 7.91; N, 21.14; P, 9.35%).

EXAMPLE 2

Tetraethyl 2-diethylamino-1,3,5-triazine-4,6-diphosphonate

To a stirred solution of hexaethyl 1,3,5-triazine- 2,4,6-triphosphonate (29.34 g, 0.06 mol) in toluene (90 ml), cooled at $-5°$ C. and protected from atmospheric moisture, was added dropwise over 25 minutes a solution of diethylamine (26.28 g, 0.36 mol) in toluene (45 ml). The resulting solution was stirred for 1 hour at 0° C., and then allowed to react for a further 3 days at 20° C. with stirring. Removal of solvent, and drying at 95° C./1 mm, gave a mobile oil (26.57 g). A solution of the oil in dichloromethane was extracted with water and dried ($Na_2SO_4$). Removal of solvent, and drying at 95° C./1.5 mm, gave the analytical sample of tetraethyl 2-diethylamino-1,3,5-triazine-4,6-diphosphonate (24.50 g, 96%) as a yellow oil, identified by $^1$H-NMR, $^{13}$C-NMR and FT-IR. $^1$H-NMR: δ ($CDCl_3$) 1.22 (6H, t, J=7 Hz, $MeCH_2N$), 1.41 (12H, t, $J_{HH}$=7 Hz, $MeCH_2$-O-P), 3.68 (4H, quartet, J=7 Hz, Me-$CH_2$-N), 4.38 (8H, doublet of quartets, $J_{HH}$=7 Hz, $J_{PH}$=7 Hz, Me-$CH_2$-O-P);
$^{13}$C-NMR: δ ($CDCl_3$) 12.2 ( s, $MeCH_2N$), 16.1 (s, $MeCH_2$O-P), 41.9 (s, Me-$CH_2$-N), 64.0 (s, Me-$CH_2$-O-P), 161.4 (t, $J_{PCNC}$=19 Hz, triazine ring carbon with nitrogen substituent), 170.6 (dd, $J_{PC}$=265 Hz, $J_{PCNC}$=15 Hz, triazine ring carbons with phosphorus substituents);
FT-IR: $v_{max}$ (neat) 3495, 2985, 2935, 2910, 1575, 1535, 1480, 1255, 1045, 1025 $cm^{-1}$.
(Analysis: Found C, 42.21; H, 7.30; N, 13.27; P, 14.89. $C_{15}H_{30}N_4O_6P_2$ requires C, 42.45; H, 7.13; N, 13.20; P, 14.60%).

EXAMPLE 3

Diethyl 2-anilino-4-pyrrolidino-1,3,5-triazine-6-phosphonate

To a stirred solution of hexaethyl 1,3,5-triazine- 2,4,6-triphosphonate (29.34 g, 0.06 mol) in toluene (90 ml), cooled at −5° C. and protected from atmospheric moisture, was added dropwise over 25 minutes a solution of aniline (5.58 g, 0.06 mol) and triethylamine (6.06 g, 0.06 mol) in toluene (30 ml). The solution was stirred for 1 hour at 0° C., and then allowed to react at 20° C. for a further 3 days. To the resulting solution, cooled with stirring at +1° C., was added dropwise over 20 minutes a solution of pyrrolidine (4.32 g, 0.06 mol) and triethylamine (6.06 g, 0.06 mol) in toluene (30 ml). The solution was stirred for 1 hour at 0° C., and then allowed to react at 20° C. for another 3 days. Removal of solvent, and drying at 95° C./1 mm, gave a damp yellow solid (25.58 g). A solution of the solid in dichloromethane was extracted with water and dried ($Na_2SO_4$). Removal of solvent, and drying at 95° C./1.5 mm, gave the crude product as a light yellow solid (22.69 g, 100%). Recrystallisation from carbon tetrachloride gave the analytical sample of diethyl 2-anilino-4-pyrrolidino-1,3,5-triazine-6-phosphonate (16.97 g, 75%) as a white solid, mp 150°–151° C., identified by $^1$H-NMR, $^{13}$C-NMR and FT-IR.
$^1$H-NMR: δ ($CDCl_3$) 1.40 (6H, t, $J_{HH}$=7 Hz, $MeCH_2$O-P), 1.94–2.01 (4H, symmetrical narrow multiplet, C-$CH_2$-C of pyrrolidine ring), 3.59–3.65 (4H, symmetrical narrow multiplet, $CH_2$-N of pyrrolidine ring), 4.36 (4H, doublet of quartets, $J_{HH}$=7 Hz, $J_{PH}$=7 Hz, Me-$CH_2$O-P), 7.04 ($^1$H, t, $J_{mp}$=8 Hz, p-hydrogens of Ph), 7.31 (2H, dd, $J_{om}$=$J_{mp}$=8 Hz, m-hydrogens of Ph), 7.40 (1H, sharp singlet, NH), 7.64 (2H, d, $J_{om}$=8 Hz, o-hydrogens of Ph);
$^{13}$C-NMR: δ ($CDCl_3$) 16.6 and 16.7 (1:1, $MeCH_2$O-P), 25.3 and 25.4 (1:1, C-$CH_2$-C of pyrrolidine ring), 46.6 and 46.7 (1:1, $CH_2$-N of pyrrolidine ring), 64.0 and 64.1 (1:1, Me-$CH_2$-O-P), 120.0, 123.3, 129.0 and 138.8 (four singlets, ca. 2:1:2:1, aromatic carbons of Ph group), 162.3 (d, $J_{PCNC}$=21 Hz) and 163.0 (d, $J_{PCNC}$=21 Hz) [triazine ring carbons with different nitrogen substituents], 170.2 (d, $J_{PC}$=266 Hz, triazine ring carbon with phosphorus substituent);
FT-IR: $v_{max}$ (neat) 3300, 2965, 2930, 2870, 1610, 1580, 1525, 1490, 1235, 1020 $cm^{-1}$.
(Analysis: Found C, 54.00; H, 6.28; N, 18.59; P, 8.21. $C_{17}H_{24}N_5O_3P$ requires C, 54.11; H, 6.41; N, 18.56; P, 8.21%).

EXAMPLE 4

Poly(diethyl N,N'-ethylene-2,4-diamino-1,3,5-triazine-6-phosphonate)

To a stirred solution of hexaethyl 1,3,5-triazine- 2,4,6-triphosphonate (146.7 g, 0.30 mol) in toluene (450 ml), cooled at +3° C. and protected from atmospheric moisture, was added dropwise over 75 minutes a solution of ethylenediamine (18.0 g, 0.30 mol) and triethylamine (60.6 g, 0.60 mol) in toluene (150 ml). The resulting solution was stirred for 70 minutes at +2° C., and then allowed to react for a further 6 days at 20° C. with stirring. Crystallised solid was removed by filtration, washed with further toluene (300 ml), then dried in vacuo. Poly(diethyl N,N'-ethylene- 2,4-diamino-1,3,5-triazine-6-phosphonate) (81.4 g, 99%) was obtained as a white solid, identified by $^1$H-NMR, $^{13}$C-NMR and FT-IR. $^1$H-NMR: δ ($CDCl_3$) 1.2–1.4 (6H, m, $MeCH_2$O-P), 3.3–3.9 (broad multiplet, $CH_2$-N) and 4.23 (m, Me-$CH_2$-O-P) [total 8H], 8.12 (ca.2H, broad singlet, NH); δ (DMSO-$d_6$) 1.25 (6H, broad singlet, $MeCH_2$O-P), 3.36 (broad singlet, $CH_2$-N and absorbed $H_2O$), 4.15 (4H, m, Me-$CH_2$-O-P), 7.4–7.9 (2H, broad multiplet, NH);
$^{13}$C-NMR: δ ($CDCl_3$) 16.3 (s, $MeCH_2$O-P), 38.9 (broad singlet, $CH_2$-N), 63.6 and 64.2 (two singlets, Me-$CH_2$-O-P), 164.1 (d, $J_{PCNC}$=20 Hz, triazine ring carbons with nitrogen substituents), 168.5 (d, $J_{PC}$=265 Hz, triazine ring carbon with phosphorus substituent);
FT-IR: $v_{max}$ (neat) 3255, 3140, 3100, 2985, 1620, 1600, 1545, 1245, 1050, 1020 $cm^{-1}$.
(Analysis: Found C, 38.34; H, 5.94; N, 23.37; P, 12.54%).

EXAMPLE 5

Poly[diethyl 2,4-(N,N'-piperazino)-1,3,5-triazine-6-phosphonate]

To a stirred solution of hexaethyl 1,3,5-triazine- 2,4,6-triphosphonate (29.34 g, 0.06 mol) in toluene (90 ml), cooled at −2° C. and protected from atmospheric moisture, was added dropwise over 40 minutes a solution of piperazine (5.16 g, 0.06 mol) and triethylamine (12.12 g, 0.12 mol) in ethanol (30 ml). The resulting solution was stirred for 1 hour at 0° C., and then allowed to react for a further 6 days at 20° C. with stirring. Removal of solvent, and drying at 95° C./1 mm, gave a light yellow powderable glass (24.00 g). A solution of the material in dichloromethane was extracted with water and dried ($Na_2SO_4$). Removal of solvent, and drying at 95° C./1.5 mm, gave poly[diethyl 2,4-(N,N'-piperazino)- 1,3,5-triazine-6- phosphonate] as a pale yellow glass (17.57 g, 98%), which was crushed to a pale yellowish-white powder, and identified by $^1$H-NMR, $^{13}$C-NMR and FT-IR.
$^1$H-NMR: δ ($CDCl_3$) 1.34–1.46 (narrow multiplet, $MeCH_2$O-P), 3.85–4.12 (m, $CH_2$-N of piperazine ring), 4.26–4.43 (m, $MeCH_2$-O-P);
$^{13}$C-NMR: δ ($CDCl_3$) 16.4 (s, $MeCH_2$O-P), 42.9 (broad singlet, $CH_2$-N of piperazine ring), 63.9 (s, Me-$CH_2$-O-P), 163.7 (d, $J_{PCNC}$=22 Hz, triazine ring carbons with nitrogen substituents), 170.3 (d, $J_{PC}$=267 Hz, triazine ring carbon with phosphorus substituent) [piperazinotriazine-phosphonate polymer backbone]; 64.3 (s, Me-$CH_2$-O-P), 162.4 (t, $J_{PCNC}$=18 Hz, triazine ring carbon with nitrogen substituent), 171.3 (dd, $J_{PC}$=264 Hz, $J_{PCNC}$=15 Hz, triazine ring carbons with phosphorus substituents) [triazine-diphosphonate end-groups];
FT-IR: $v_{max}$ (neat) 3485, 2985, 2925, 2865, 1545, 1495, 1445, 1250, 1220, 1025 $cm^{-1}$.

(Analysis: Found C, 40.74; H, 6.35; N, 17.54; P, 13.20%).

Reaction of a stirred mixture of hexaethyl 1,3,5-triazine-2,4,6-triphosphonate (48.90 g, 0.10 mol) and piperazine (8.61 g, 0.10 mol) at 120° C. for 6 hours in the absence of solvent, followed by aqueous washing of a chloroform solution of the resulting gum, removal of solvent and drying, afforded a shorter-chain variant of the same polymer as a pale yellow glassy gum (21.51 g, 72%), identified by $^1$H-NMR, $^{13}$C-NMR and FT-IR.

EXAMPLE 6

Diethyl 2,4-diamino-1,3,5-triazine-6-phosphonate

Reaction of hexaethyl 1,3,5-triazine-2,4,6-triphosphonate and ammonia in ethanol gave diethyl 2,4-diamino- 1,3,5-triazine-6-phosphonate as a white solid (yield 77%), mp 273°–274° C. (decomp.), identified by $^1$H-NMR, $^{13}$C-NMR and FT-IR.

(Analysis: Found C, 34.45; H, 5.45; N, 28.47; P, 12.98. $C_7H_{14}N_5O_3P$ requires C, 34.01; H, 5.71; N, 28.33; P, 12.53%).

Flexible polyurethane foam, of density 32.8 kg m$^{-3}$ and containing 3.0% w/w of diethyl diaminotriazinephosphonate (DDTP), was made from Shell Caradol 48-2 polyol, containing DDTP (4.5 parts per hundred), plus 2,4-/2,6-tolylene diisocyanate (isomer ratio 80:20). Assessment of the horizontal burning characteristics of foam strips of dimensions 150 mm×50 mm×13 mm was carried out in accordance with the BS 4735 combustion test. For 10 strips, the mean time to burn a distance of 125 mm was 81.6 seconds, and hence the mean burn rate was 1.5 mm sec$^{-1}$. For foam of the same mean density, containing the chlorinated flame retardant tris-(2-chloroethyl) phosphate at the same level (3.0% w/w) instead of DDTP, the time to burn 125 mm was 80.6 seconds and the burn rate was 1.5 mm sec$^{-1}$. The corresponding figures for 20 foam strips of the same mean density, containing no flame retardant but otherwise identical, were 48.3 seconds and 2.6 mm sec$^{-1}$.

EXAMPLE 7

Diethyl 2,4-bis(isopropylamino)-1,3,5-triazine-6-phosphonate

To a stirred solution of cyanuric chloride (9.22 g, 0.05 mol) in toluene (45 ml) at 53° C., protected from atmospheric moisture, was added dropwise with gentle warming a solution of triethyl phosphite (16.60 g, 0.10 mol, 2 equivalents) in toluene (30 ml) over a period of 30 minutes, during which the temperature increased to 97° C. Heat input was increased, and the temperature was raised to reflux (115° C.) over 50 minutes. The reaction mixture was then heated under reflux, with collection of ethyl chloride (5.3 ml, 75%), for a further 2 hours. After cooling the resulting solution for 30 minutes, a solution of isopropylamine (17.75 g, 0.30 mol) in toluene (25 ml) was added dropwise over 55 minutes at −3° C. The reaction mixture was warmed to 45° C. over 15 minutes, and maintained at 47° C. for a further 70 minutes. After cooling to 20° C., dichloromethane and water were added to the reaction mixture, and the separated organic phase was extracted with water and dried (Na$_2$SO$_4$). Removal of solvent, and drying at 95° C./1.5 mm, gave diethyl 2,4-bis(isopropylamino)-1,3,5-triazine- 6-phosphonate (15.10 g, 91%) as a yellowish-white solid, mp 91°–94° C. identified by $^1$H-NMR, $^{13}$C-NMR, FT-IR, and TLC comparison with the authentic sample produced in Example 1. The residual chlorine content was only 0.16% w/w, and no 2-chloro-4,6-bis(isopropylamino)- 1,3,5-triazine or other significant impurities were detected by TLC.

EXAMPLE 8

Diethyl 2,4-bis(isopropylamino)-1,3,5-triazine-6-phosphonate

To a stirred solution of cyanuric chloride (18.45 g, 0.10 mol) in toluene (90 ml) at 56° C., protected from atmospheric moisture, was added dropwise with gentle warming a solution of triethyl phosphite (16.60 g, 0.10 mol, 1 equivalent) in toluene (60 ml) over a period of 30 minutes, during which the temperature increased to 98° C. Heat input was increased, and the temperature was raised to reflux (116° C.) over 35 minutes. The reaction mixture was then heated under reflux, with collection of ethyl chloride (5.3 ml, 75%), for a further 2 hours. After cooling the resulting solution for 30 minutes, a solution of isopropylamine (35.50 g, 0.60 mol) in toluene (50 ml) was added dropwise over 80 minutes at +1° C. The reaction mixture was warmed to 40° C. over 25 minutes, and maintained at 46° C. for a further 70 minutes. After cooling to 20° C., dichloromethane and water were added to the reaction mixture, and the separated organic phase was extracted with water and dried (Na$_2$SO$_4$). Removal of solvent, and drying at 95° C./1 mm, gave a stiff gum (28.47 g), which was separated into a white powder and a pale yellow gum by treatment with diisopropyl ether. The products, identified by a combination of $^1$H-NMR, $^{13}$C-NMR, FT-IR, TLC and elemental analysis, were diethyl 2,4-bis(isopropylamino)-1,3,5-triazine- 6-phosphonate (yield 76%), 2-chloro-4,6-bis(isopropylamino)- 1,3,5-triazine (yield 15%), and a trace of N,N',N"-triisopropylmelamine.

Similar reactions, in which 1,1,1-trichloroethane (reflux 75° C.) and 1,4-dioxan (reflux 105° C.) were used as solvents instead of toluene, both gave diethyl 2,4-bis(isopropylamino)- 1,3,5-triazine-6-phosphonate in 81% yield, together with 2-chloro-4,6-bis(isopropylamino)-1,3,5-triazine (yield 12–17%).

The reaction between cyanuric chloride and triethyl phosphite can be carried out in the absence of solvent if desired. The subsequent reaction with an amine is, however, preferably carried out in a solvent to moderate the exothermic reaction.

EXAMPLE 9

Diethyl 2,4-bis(diethylamino)-1,3,5-triazine-6-phosphonate

A solution in diethylamine (125 ml, 88.4 g, 1.2 mol) of tetraethyl 2-diethylamino-1,3,5-triazine-4,6-diphosphonate (25.44 g, 0.06 mol), produced according to Example 2, was heated under reflux at 59° C. for 36 hours with stirring, until TLC indicated complete consumption of starting material. The reaction mixture, consisting of a pale yellow liquid with much crystalline solid, was allowed to cool to 20° C., and then dissolved in dichloromethane (60 ml). Removal of solvent and excess diethylamine, and drying at 95° C./1 mm, gave a damp yellow solid (30.38 g). A solution of the solid in toluene was extracted with water and dried (Na$_2$SO$_4$). Removal of solvent, and drying at 95° C./1.5 mm, gave diethyl 2,4-bis(diethylamino)-1,3,5-triazine-6-phosphonate (11.40 g, 53%) as a waxy solid, identified by $^1$H-NMR, $^{13}$C-NMR and FT-IR. Recrystallisation from n-hexane at −78° C. gave the analytical sample (10.49 g, 49%) as light yellow crystals, mp 45°–46° C.
(Analysis: Found C, 50.10; H, 8.54; N, 19.43; P, 8.63. $C_{15}H_{30}N_5O_3P$ requires C, 50.13; H, 8.41; N, 19.49; P, 8.62%).

EXAMPLE 10

Diethyl 2,4-bis-(n-butylamino)-1,3,5-triazine-6-phosphonate

Reaction of hexaethyl 1,3,5-triazine-2,4,6-triphosphonate (29.34 g, 0.06 mol) and n-butylamine (26.28 g, 0.36 mol) in toluene (total 135 ml), according to the procedure described in Example 1, on removal of solvent gave a soft grey gum (23.75 g). Aqueous washing of a dichloromethane solution, removal of solvent and drying afforded the analytical sample of diethyl 2,4-bis-(n-butylamino)- 1,3,5-triazine-6-phosphonate (21.49 g, 100%) as a colourless syrup, identified by $^1$H-NMR $^{13}$C-NMR and FT-IR.
(Analysis: Found C, 50.01; H, 8.19; N, 18.65; P, 8.79. $C_{15}H_{30}N_5O_3P$ requires C, 50.13; H, 8.41; N, 19.49; P, 8.62%).

EXAMPLE 11

Diethyl 2,4-dipiperidino-1,3,5-triazine-6-phosphonate

Reaction of hexaethyl 1,3,5-triazine-2,4,6-triphosphonate (29.34 g, 0.06 mol) and piperidine (30.60 g, 0.36 mol) in toluene (total 135 ml), according to the procedure described in Example 1, on removal of solvent gave a pale pink solid (26.52 g). Aqueous washing of a dichloromethane solution, removal of solvent and drying afforded diethyl 2,4-dipiperidino-1,3,5-triazine-6-phosphonate (23.43 g, 100%), identified by $^1$H-NMR, $^{13}$C-NMR and FT-IR. Recrystallisation from cyclohexane gave the analytical sample (22.50 g, 98%) as white crystals, mp 103°– 105° C.
(Analysis: Found C, 52.78; H, 8.10; N, 17.88; P, 8.13. $C_{17}H_{30}N_5O_3P$ requires C, 53.25; H, 7.89; N, 18.26; P, 8.08%).

Reaction occurs readily according to the procedure described herein, which is contrary to the claim by Hewertson, Shaw and Smith, in J. Chem. Soc., 1963, 1670–1675, that these authors found no reaction of the same starting materials under similar conditions.

EXAMPLE 12

Diethyl 2,4-dimorpholino-1,3,5-triazine-6-phosphonate

Reaction of hexaethyl 1,3,5-triazine-2,4,6-triphosphonate (29.34 g, 0.06 mol) and morpholine (31.32 g, 0.36 mol) in toluene (total 135 ml), according to the procedure described in Example 1, on removal of solvent gave a pale yellow solid (26.39 g). Aqueous washing of a dichloromethane solution, removal of solvent and drying afforded diethyl 2,4-dimorpholino-1,3,5-triazine-6-phosphonate (22.76 g 98%), identified by $^1$H-NMR, $^{13}$C-NMR and FT-IR. Recrystallisation from cyclohexane/toluene (5:1 v/v) gave the analytical sample (22.02 g, 95%) as white crystals, mp 114°–116° C.
(Analysis: Found C, 46.36; H, 6.87; N, 17.98; P, 7.98. $C_{15}H_{26}N_5O_5P$ requires C, 46.51; H, 6.77; N, 18.08; P, 8.00%).

EXAMPLE 13

Diethyl 2,4-dipyrrolidino-1,3,5-triazine-6-phosphonate

Reaction of hexaethyl 1,3,5-triazine-2,4,6-triphosphonate (29.34 g, 0.06 mol) and pyrrolidine (25.56 g, 0.36 mol) in toluene (total 135 ml), according to the procedure described in Example 1, on removal of solvent gave a pale grey solid (25.44 g). Aqueous washing of a dichloromethane solution, removal of solvent and drying afforded diethyl 2,4-dipyrrolidino-1,3,5-triazine-6-phosphonate (21.71 g, 100%), identified by $^1$H-NMR, $^{13}$C-NMR and FT-IR. Recrystallisation from cyclohexane gave the analytical sample (20.17 g, 95%) as a pale brown solid, mp 65°–69° C.
(Analysis: Found C, 49.89; H, 7.44; N, 19.16; P, 9.05. $C_{15}H_{26}N_5O_3P$ requires C, 50.70; H, 7.37; N, 19.71; P, 8.72%).

EXAMPLE 14

Tetraethyl 2-bis-(2'-ethylhexyl)amino-1,3,5-triazine-4,6-diphosphonate

Reaction of hexaethyl 1,3,5-triazine-2,4,6-triphosphonate (29.34 g, 0.06 mol), di-2-ethylhexylamine (14.46 g, 0.06 mol) and triethylamine (6.06 g, 0.06 mol) in toluene (total 135 ml), according to the procedure described in Example 2, on removal of solvent gave a solid/liquid mixture (39.60 g). Aqueous washing of a toluene solution, removal of solvent and drying afforded the analytical sample of tetraethyl 2-bis-(2'-ethylhexyl)amino-1,3,5-triazine-4,6-diphosphonate (29.37 g, 83%) as a red viscous oil, identified by $^1$H-NMR, $^{13}$C-NMR and FT-IR.
(Analysis: Found C, 54.80; H, 9.43; N, 8.59; P, 10.24. $C_{27}H_{54}N_4O_6P_2$ requires C, 54.72; H, 9.18; N, 9.45; P, 10.45%).

EXAMPLE 15

Tetraethyl 2-anilino-1,3,5-triazine-4,6-diphosphonate

Reaction of hexaethyl 1,3,5-triazine-2,4,6-triphosphonate (29.34 g, 0.06 mol), aniline (5.58 g, 0.06 mol) and triethylamine (6.06 g, 0.06 mol) in toluene (total 135 ml), according to the procedure described in Example 2, on removal of solvent gave a soft yellow gum (28.49 g). Aqueous washing of a dichloromethane solution, removal of solvent and drying afforded tetraethyl 2-anilino-1,3,5-triazine-4,6-diphosphonate (26.02 g, 98%) as a yellow viscous syrup, identified by $^1$H-NMR, $^{13}$C-NMR and FT-IR.

An otherwise identical reaction in which double quantities of aniline (11.16 g, 0.12 mol) and triethylamine (12.12 g, 0.12 mol) were used and aqueous washing of the crude product was carried out in toluene solvent instead of dichloromethane, also gave tetraethyl 2-anilino-1,3,5-triazine- 4,6-diphosphonate (21.90 g, 82%), which was identified by $^1$H-NMR, $^{13}$C-NMR and FT-IR. (Analysis: Found C, 45.61; H, 5.83; N, 12.34; P, 13.76. $C_{17}H_{26}N_4O_6P_2$ requires C, 45.95; H, 5.90; N, 12.61; P, 13.94%).

EXAMPLE 16

Tetraethyl 2-pyrrolidino-1,3,5-triazine-4,6-diphosphonate

Reaction of hexaethyl 1,3,5-triazine-2,4,6-triphosphonate (29.34 g, 0.06 mol), pyrrolidine (4.26 g, 0.06 mol) and triethylamine (12.12 g, 0.12 mol) in toluene (total 150 ml), according to the procedure described in Example 2, on removal of solvent gave a mobile oil (26.27 g). Aqueous washing of a dichloromethane solution, removal of solvent and drying afforded tetraethyl 2-pyrrolidino-1,3,5-triazine-4,6-diphosphonate (24.49 g, 97%) as a pale yellow oil, identified by $^1$H-NMR, $^{13}$C-NMR and FT-IR.

(Analysis: Found C, 42.49; H, 6.59; N, 13.21; P, 14.25. $C_{15}H_{28}N_4O_6P_2$ requires C, 42.66; H, 6.68; N, 13.27; P, 14.67%).

An otherwise identical reaction in which diethylamine (4.38 g, 0.06 mol) was added 1 hour after the pyrrolidine (at +1° C.) also gave tetraethyl 2-pyrrolidino-1,3,5-triazine-4,6-diphosphonate in the same yield.

EXAMPLE 17

Tetraethyl 2-n-butylamino-1,3,5-triazine-4,6-diphosphonate

Reaction of hexaethyl 1,3,5-triazine-2,4,6-triphosphonate (29.34 g, 0.06 mol), n-butylamine (4.38 g, 0.06 mol) and triethylamine (12.12 g, 0.12 mol) in toluene (total 150 ml), according to the procedure described in Example 2 except for a reaction time of 6 days, on removal of solvent gave a mobile oil (26.21 g). Aqueous washing of a dichloromethane solution, removal of solvent and drying afforded tetraethyl 2-n-butylamino-1,3,5-triazine-4,6-diphosphonate (24.07 g, 95%) as a pale yellow oil, identified by $^1$H-NMR $^{13}$C-NMR and FT-IR (Analysis: Found C, 42.40; H, 7.10; N, 13.30; P, 14.56. $C_{15}H_{30}N_4O_6P_2$ requires C, 42.45; H, 7.13; N, 13.20; P, 14.60%).

An otherwise identical reaction in which diethylamine (4.38 g, 0.06 mol) was added 1 hour after the n-butylamine (at 0° C.) also gave tetraethyl 2-n-butylamino-1,3,5-triazine-4,6-diphosphonate in 87% yield.

EXAMPLE 18

Diethyl 2-n-butylamino-4-diethylamino-1,3,5-triazine-6-phosphonate

Tetraethyl 2-n-butylamino-1,3,5-triazine-4,6-diphosphonate prepared as described in Example 17 was dissolved in excess diethylamine and heated at reflux (59°–60° C.) for 6 hours to produce diethyl 2-n-butylamino-4-diethylamino-1,3,5-triazine-6-phosphonate.

EXAMPLE 19

Diisopropyl 2,4-diamino-1,3,5-triazine-6-phosphonate

To a stirred solution of anhydrous ammonia (12.5 ml liquid, 8.5 g, 0.5 mol) in isopropanol (70 ml), cooled at –5° C. and protected from atmospheric moisture, was added dropwise over 20 minutes a solution of hexaisopropyl 1,3,5-triazine- 2,4,6-triphosphonate (25.70 g, 0.045 mol) in isopropanol (40 ml). The reaction mixture was warmed to 18° C., and then allowed to react for a further 3 days at 18° C. with stirring. Crystallised solid was removed by filtration, washed with water and acetone and then dried in vacuo. Diisopropyl 2,4-diamino- 1,3,5-triazine-6-phosphonate (1.87 g, 15%) was obtained as a yellowish-white solid, mp >400° C., identified by $^1$H-NMR, $^{13}$C-NMR and FT-IR.

(Analysis: Found C, 39.64; H, 6.53; N, 24.83; P, 10.95. $C_9H_{18}N_5O_3P$ requires C, 39.27; H, 6.59; N, 25.44; P, 11.25%).

Evaporation of the mother liquor, and drying at 95° C./1 mm, gave a waxy solid (14.96 g). A solution of the solid in dichloromethane was extracted with water and dried ($Na_2SO_4$). Removal of solvent, and drying at 95° C./0.3 mm, gave tetraisopropyl 2-amino-1,3,5-triazine-4,6-diphosphonate (11.91 g, 63%) as a yellowish-white solid, identified by $^1$H-NMR, $^{13}$C-NMR and FT-IR. Recrystallisation from diisopropyl ether/toluene (4:1 v/v) gave the product as white crystals, mp 123°–124° C.

(Analysis: Found C, 42.54; H, 6.98; N, 12.67; P, 13.81. $C_{15}H_{30}N_4O_6P_2$ requires C, 42.45; H, 7.13; N, 13.20; P, 14.60%).

EXAMPLE 20

Tetraisopropyl 2-amino-1,3,5-triazine-4,6-diphosphonate

To a stirred solution of hexaisopropyl 1,3,5-triazine-2,4,6-triphosphonate (42.98 g, 0.075 mol) in isopropanol (105 ml), cooled at –6° C. and protected from atmospheric moisture, was added dropwise over 10 minutes a mixture of aqueous ammonia (35% w/w, 21.86 g, 7.65 g $NH_3$, 0.450 mol) and isopropanol (33 ml). The resulting solution was stirred for 1 hour at –2° C., and then allowed to react for a further 3 days at 18° C. with stirring. Removal of solvent, and drying at 95° C./1 mm, gave a stiff gum (38.41 g). A solution of the gum in dichloromethane was extracted with water and dried ($Na_2SO_4$). Removal of solvent, and drying at 95° C./0.4 mm, gave tetraisopropyl 2-amino-1,3,5-triazine-4,6-diphosphonate as a yellowish-white solid (25.06 g, 79%), which was shown by $^1$H-NMR, $^{13}$C-NMR, FT-IR, TLC and mixed melting point to be identical with the sample of tetraisopropyl 2-amino-1,3,5-triazine-4,6- diphosphonate produced in Example 19.

EXAMPLE 21

Tetraisopropyl 2-dimethylamino-1,3,5-triazine-4,16-diphosphonate

Following the procedure of Example 20, aqueous dimethylamine (40% w/w, 50.63 g, 20.25 g $(CH_3)_2NH$, 0.450 mol) was reacted with hexaisopropyl 1,3,5-triazine-2,4,6-triphosphonate (42.98 g) to produce tetraisopropyl 2-dimethylamino- 1,3,5-triazine-4,6-diphosphonate.

EXAMPLE 22

Di-n-butyl 2,4-diamino-1,3,5-triazine-6-phosphonate

To a stirred solution of anhydrous ammonia (12.5 ml liquid, 8.5 g, 0.5 mol) in n-butanol (70 ml), cooled at –6° C. and protected from atmospheric moisture, was added dropwise over 15 minutes a solution of hexa-n-butyl 1,3,5-triazine- 2,4,6-triphosphonate (32.85 g, 0.05 mol) in n-butanol (40 ml). The reaction mixture was warmed to 18° C., and then allowed to react for a further 3 days at 18° C. with stirring. Crystallised solid was removed by filtration, washed with water and acetone, and then dried in vacuo. Di-n-butyl 2,4-diamino- 1,3,5-triazine-6-phosphonate (11.54 g, 76%) was obtained as a white solid, mp 303°–307° C. (decomp.), identified by $^1$H-NMR, $^{13}$C-NMR and FT-IR.

(Analysis: Found C, 43.66; H, 7.15; N, 23.56; P, 10.04. $C_{11}H_{22}N_5O_3P$ requires C, 43.56; H, 7.31; N, 23.09; P, 10.21%).

EXAMPLE 23

Combustion Tests of Polyurethane Foams containing Amino Triazine Phosphonates Rigid polyurethane foam, of density 40 kg m$^{-3}$ and containing 6.2% w/w of amino triazine phosphonate, was made from ICI "PBA 6919" polyol, containing amino triazine phosphonate (15 parts per hundred), plus ICI "Suprasec 5005" p,p'-methylenediphenyl diisocyanate (MDI). Assessment of the horizontal burning characteristics of foam strips was carried out as described in Example 6, in accordance with the BS 4735 combustion test. Where flame became extinguished without total burn-out of specimens, the extent of combustion quoted refers to the average of percentage distance burnt and percentage weight lost. For 10 foam strips of density 40 kg m$^{-3}$ containing 6.2% w/w of diethyl diaminotriazinephosphonate [DDTP], the extent of combustion was 19% and the mean burn rate was 0.6 mm sec$^{-1}$. For 10 foam strips of density 41 kg m$^{-3}$ containing 6.2% w/w of tetraethyl diethylaminotriazinediphosphonate [TDTDP], the extent of combustion was 29% and the mean burn rate was 0.9 mm sec$^{-1}$. For foam of density 39 kg m$^{-3}$ containing no flame retardant but otherwise identical, the extent of combustion was 100% (total burn-out) and the burn rate was 2.3 mm sec$^{-1}$.

The flame retardant performances of several amino triazine phosphonates were compared with those of the commercial chloroalkyl phosphate flame retardants tris-(2-chloroethyl) phosphate [TCEP] and tris-(1-chloro-2-propyl) phosphate [TCPP] in rigid polyurethane foam. The foam, of mean density 38 kg m$^{-3}$ and containing 4.1% w/w of amino triazine phosphonate or chloroalkyl phosphate, was made from PBA 6919 polyol, containing the appropriate phosphorus ester (10 parts per hundred), plus Suprasec 5005 MDI, and combustion tests were carried out in an identical manner to those previously described. The amino triazine phosphonates tested were diethyl diaminotriazinephosphonate [DDTP] (Example 6), poly(diethyl ethylenediaminotriazinephosphonate) [pDEDTP] (Example 4), diethyl bis(isopropylamino)triazinephosphonate [DBITP] (Example 1), diethyl bis-(n-butylamino)triazinephosphonate [DBNTP] (Example 10) and tetraethyl diethylaminotriazinediphosphonate [TDTDP] (Example 2). The extent of combustion and rate of burn for the amino triazine phosphonates and for TCPP are expressed relative to the corresponding figures for TCEP in the following Table.

| BS4735 Combustion Tests of Polyurethane Foam containing Phosphorus Esters | | | | | | | |
|---|---|---|---|---|---|---|---|
| | TCEP | TCPP | DDTP | pDEDTP | DBITP | DBNTP | TDTDP |
| Relative Extent of Combustion | 1.00 | 1.11 | 0.94 | 0.94 | 1.01 | 1.11 | 1.00 |
| Relative Rate of Burn | 1.00 | 1.23 | 0.95 | 1.02 | 0.97 | 1.06 | 0.85 |

The flame retardant performances of DDTP, pDEDTP, DBITP, DBNTP and TDTDP are at least as good as those of TCEP and TCPP under these conditions.

I claim:

1. (Twice amended) A plastics material containing a phosphorus-containing heterocyclic flame retardant, wherein the flame retardant is a sym-triazine compound of the formula:

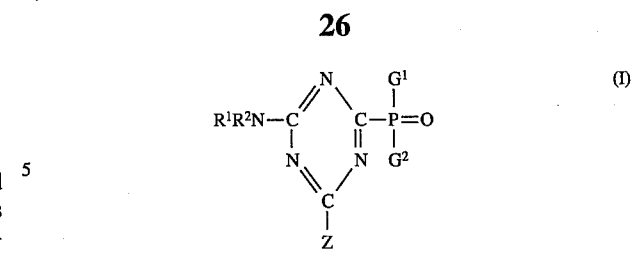

where R$^1$ represents an alkyl group having 1 to 12 carbon atoms, and R$^2$ represents an alkyl group having 1 to 12 carbon atoms;

G$^1$ and G$^2$ are each independently selected from an -OR$^3$ group, an amine group of the formula -NR$^4$R$^5$, an -OH group or an anionic group -O$^-$ in the form of a metal salt or an amine or ammonium salt, where R$^3$ represents an alkyl or cycloalkyl group having 1 to 12 carbon atoms, and R$^4$ and R$^5$ each independently represent hydrogen or an alkyl or cycloalkyl group having 1 to 12 carbon atoms;

Z represents an amine group of the formula -NR$^6$R$^7$ or a phosphonic group of the formula:

where G$^1$ and G$^2$ are defined as above;

R$^6$ represents an alkyl group having 1 to 12 carbon atoms, and R$^7$ represents an alkyl group having 1 to 12 carbon atoms.

2. A plastics material according to claim 1, wherein the plastics material is a polyurethane foam and the flame retardant is a sym-triazine compound of formula (I) in which G$^1$ and G$^2$ are each -OR$^3$ groups in which R$^3$ is an alkyl group having 2 to 6 carbon atoms.

3. A polyurethane foam according to claim 2, wherein the flame retardant is a sym-triazine compound of formula (I) in which Z is a group of the formula -NR$^6$R$^7$ and R$^1$ is an alkyl group having 1 to 6 carbon atoms.

4. A plastics material according to claim 1, wherein the plastics material is a polyester, polyamide, acrylic ester polymer, vinyl ester polymer or nitrile polymer and the flame retardant is a sym-triazine compound of formula (I) in which G$^1$ and G$^2$ are each -OR$^3$ groups in which R$^3$ is an alkyl group having 2 to 6 carbon atoms.

5. The plastics material according to claim 1, wherein the flame retardant is a sym-triazine compound which is liquid at-ambient temperature, is soluble in a polyoxypropylene triol of molecular weight 3500 and has the formula:

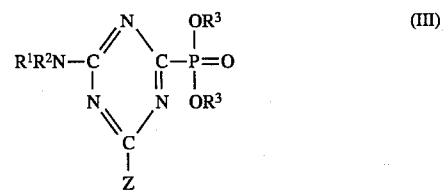

where $R^1$ represents an alkyl group having 1 to 12 carbon atoms, and $R^2$ represents an alkyl group having 1 to 12 carbon atoms;

each group $R^3$, which may be the same or different, represents an alkyl group having 1 to 6 carbon atoms; and Z represents an amine group of the formula $-NR^6R^7$ or a phosphonate group of the formula:

$$\begin{array}{c} OR^3 \\ | \\ -P=O \\ | \\ OR^3 \end{array}$$

where $R^3$ is defined as above; $R^6$ represents an alkyl group having 1 to 12 carbon atoms, and $R^7$ represents an alkyl group having 1 to 12 carbon atoms.

6. The plastics material according to claim 5, wherein in the formula III, Z represents a group of the formula $-NR^6R^7$, and the total number of carbon atoms in the groups $R^1$, $R^2$, $R^6$ and $R^7$ is 4 to 8 carbon atoms.

7. The plastics material according to claim 5, wherein in the formula III, the groups $-NR^1R^2$ and $-NR^6R^7$ are different.

8. The plastics material according to claim 1, wherein the flame retardant is diethyl 2,4-bis(diethylamino)- 1,3,5-triazine-6-phosphonate.

9. The plastics material according to claim 1 wherein the flame retardant is tetraethyl 2-diethylamino- 1,3,5-triazine-4,6-diphosphonate.

10. The plastics material according to claim 1 wherein, in the formula (I), $G^1$ and $G^2$ each represent a group of the formula $-OR^3$ and Z represents a group of the formula $$\begin{array}{c} OR^3 \\ | \\ -P=O \\ | \\ OR^3 \end{array}$$

11. The plastics material according to claim 1, wherein the plastics material is thermoset.

* * * * *

UNITED STATES PATENT AND TRADEMARK OFFICE
CERTIFICATE OF CORRECTION

PATENT NO. : 5,534,573
DATED : July 9, 1996
INVENTOR(S) : Jonathan Leake

It is certified that error appears in the above-indentified patent and that said Letters Patent is hereby corrected as shown below:

In the Abstract, delete "phosphonate" in both occurrences and insert in place thereof -- phosphonic --.

Col. 6, line 10, in the formula, delete "$R^3O=P=O$" and insert in place thereof -- $R^3O-P=O$ --.

Col. 13/14, in the equation, in the third compound, insert the missing bonds.

Col. 16, line 40, delete "multipiers" and insert in place thereof -- multiplets --.

Col. 16, line 40, delete "($^1H$," and insert in place thereof -- (1H, --.

Col. 17, line 50, delete "($^1H$," and insert in place thereof -- (1H, --.

Col. 24, line 41, delete "2-dimethylamino-1,3,5-triazine-4,16-diphosphonate and insert in place thereof -- 2-dimethylamino-1,3,5-triazine-4,6-diphosphonate --.

Col. 25, in Claim 1, delete "(Twice amended)".

Signed and Sealed this

Seventeenth Day of December, 1996

Attest:

BRUCE LEHMAN

Attesting Officer

Commissioner of Patents and Trademarks